Figure 1:
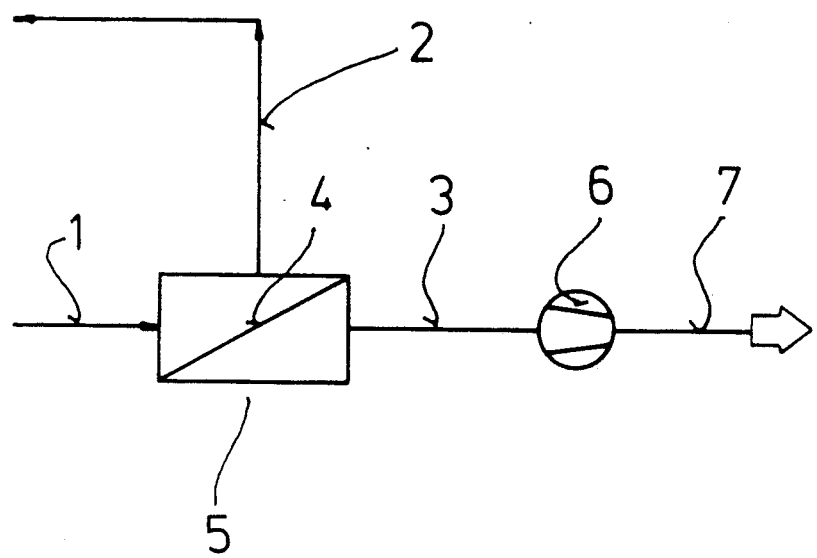

United States Patent [19]

Spiske et al.

[11] Patent Number: 5,051,188

[45] Date of Patent: Sep. 24, 1991

[54] REMOVAL OF WATER FROM A MIXTURE OF WATER, $CO_2$ AND AMINES

[75] Inventors: Luise Spiske, Seeheim-Jugenheim; Dietrich Luetzow, Limburgerhof; Christof Herion, Ladenburg; Klaus Kuessner, Frankenthal; Werner Hefner, Lampertheim, all of Fed. Rep. of Germany

[73] Assignee: BASF Aktiengesellschaft, Ludwigshafen, Fed. Rep. of Germany

[21] Appl. No.: 606,325

[22] Filed: Oct. 31, 1990

[30] Foreign Application Priority Data

Nov. 14, 1989 [DE] Fed. Rep. of Germany ....... 3937796

[51] Int. Cl.$^5$ ................................................ B01D 13/00
[52] U.S. Cl. ..................................... 210/640; 210/650; 210/651; 210/653; 210/500.23; 210/500.27; 55/16
[58] Field of Search .............. 210/640, 500.22, 500.23, 210/500.27, 500.42, 500.21, 650, 651, 653, 654; 203/11; 55/16

[56] References Cited

U.S. PATENT DOCUMENTS

| | | | |
|---|---|---|---|
| 3,288,686 | 7/1963 | Otmer | 203/11 |
| 3,750,735 | 8/1973 | Chiang et al. | 210/640 |
| 3,869,351 | 3/1975 | Schwartzman | 203/11 |
| 4,725,359 | 2/1988 | Ray | 210/640 |
| 4,755,299 | 7/1988 | Brüschke | 210/640 |
| 4,875,980 | 10/1989 | Arita et al. | 210/640 |
| 4,900,626 | 2/1990 | Fabre | 210/500.23 |

FOREIGN PATENT DOCUMENTS

| | | |
|---|---|---|
| 937586 | 1/1956 | Fed. Rep. of Germany . |
| 1768256 | 10/1971 | Fed. Rep. of Germany . |
| 3529175 | 2/1987 | Fed. Rep. of Germany . |

Primary Examiner—Robert A. Dawson
Assistant Examiner—Ana Fortuna
Attorney, Agent, or Firm—Keil & Weinkauf

[57] ABSTRACT

Water is removed from a mixture containing water, $CO_2$ and one or more amines by pervaporation by bringing the mixture into contact with one side of a membrane and removing the water-containing permeate as a vapor from the other side of the membrane.

7 Claims, 3 Drawing Sheets

REMOVAL OF WATER FROM A MIXTURE OF WATER, CO₂ AND AMINES

The present invention relates to a process for removing water from a mixture of water, $CO_2$ and one or more amines by pervaporation.

In chemical processes where water is formed as well as the desired product, it is generally necessary, if unconverted starting material is to be recycled into the reactor, to bleed off a side stream from the recycle stream to stop the water content of the recycle stream from rising too much, since this can reduce the conversion into the desired product. The bleed stream, in addition to water, generally contains starting materials, which are separated from the water and recycled into the reactor. This separation can be effected for example by distillation.

However, such a distillative separation of a bleed stream is problematical if such a bleed stream, in addition to water, contains amines as recoverable starting materials and $CO_2$. Such an amine-, water- and $CO_2$-containing bleed stream is obtained for example in the preparation of dialkylureas by reaction of excess monoalkylamines with $CO_2$ (e.g. DE-C-937,586 and DE-C-1,768,256). The distillative separation of these bleed streams gives $CO_2$ and the amines as head product. As the head product cools, however, there is a danger that solid carbamate will become deposited, which may cause appreciable technical problems.

DE-C-1,768,256 discloses avoiding carbamate formation by treating the amine-, $CO_2$- and water-containing stream in the distillation column with sodium hydroxide solution, causing the $CO_2$ to become bound as sodium carbonate, which is eliminated from the distillation column as an aqueous solution. It is a disadvantage of this process that appreciable quantities of sodium hydroxide solution are required for binding the $CO_2$ and that the disposal or reuse of the aqueous sodium carbonate solution obtained can be problematical.

It is an object of the present invention to provide a process for separating water from water-, $CO_2$-and amine-containing mixtures which avoids or reduces the disadvantages of existing processes.

We have found that this object is achieved by an advantageous process for separating water from a mixture containing water, $CO_2$ and one or more amines by separating water from the mixture through pervaporation by bringing the mixture into contact with one side of a membrane and removing the water-containing permeate as a vapor from the other side of the membrane.

The novel process makes it possible to separate water from a water-, $CO_2$- and amine-containing mixture in a simple manner. There is no need in the water removal process according to the present invention to bind the $CO_2$ by adding alkali metal hydroxide solution.

The process according to the present invention is in general carried out using a water-selective membrane. Owing to the amine content of the mixture to be separated, it is advantageous to use base-resistant membranes.

Suitable membranes are for example nonporous membranes based on polyvinyl alcohol.

Suitable apparatus for the pervaporative separation of mixtures by the process according to the present invention contains for example a crude mixture compartment for the mixture to be separated, a permeate compartment for the removed permeate and a membrane in between together with at least one inflow channel connected to the crude mixture compartment and at least one outflow channel connected to the permeate compartment (cf. for example DE-A-3,529,175). The crude mixture compartment advantageously further contains an outflow channel for that part of the mixture (retentate) held back or retained by the membrane.

The pervaporation process according to the present invention is advantageously carried out in such a way that the concentration of water in the permeate is higher than the concentration of water in the feed mixture and that the amine concentration, based on free amine and carbamate amine, and the $CO_2$ concentration, including carbamate $CO_2$, are lower in the permeate than in the feed mixture.

The permeate obtained in vapor form on the permeate side of the membrane can be transported away as such, i.e. in vapor form. However, it can also be advantageous to condense the permeate vapor obtained and to pass it away in liquid form. The condensation process can take place in one or more downstream condensation stages. If a plurality of downstream condensation stages are used, it can be advantageous to use different pressures and/or temperatures in the individual condensation stages. By varying process conditions such as pressure and/or temperature it is possible to fractionate the permeate, making it possible to obtain permeate main and bleed streams having different compositions.

It can also be advantageous to compress the uncondensed permeate obtained from an upstream condensation stage and to pass it on in vapor form.

The novel process is used for removing water from a mixture of water, $CO_2$ and one or more amines, which can be primary, secondary or tertiary. Preference is given to using mixtures containing secondary amines and in particular primary amines. It is advantageous for the amines to be alkylamines of from 1 to 8 carbon atoms, preferably from 1 to 6 carbon atoms, in particular from 1 to 3 carbon atoms, in the alkyl groups, which in the case of the secondary and tertiary amines may be identical or different. Suitable amines are for example methylamine, ethylamine, propylamine, hexylamine, dimethylamine, diethylamine, methylisopropylamine and trimethylamine.

In what follows, further details of the present invention are illustrated with reference to embodiment examples whose flow diagrams are diagrammatically depicted in FIGS. 1 to 3, where

- 5 denotes an apparatus for separating the $CO_2$/$H_2O$/amine mixture by pervaporation (the pervaporator),
- 4 the membrane in the pervaporator,
- 1 the inflow line for feed mixture,
- 2 the outflow line for retentate and
- 3 the outflow line for permeate.

According to FIG. 1, the permeate vapor produced in the pervaporator 5 is transported away in vapor form via a pressure-regulated vacuum pump 6, which maintains a constant pressure, and line 7. Under otherwise constant conditions the composition of the permeate is determined by the permeate pressure preset via the pressure regulator.

Figure 2:
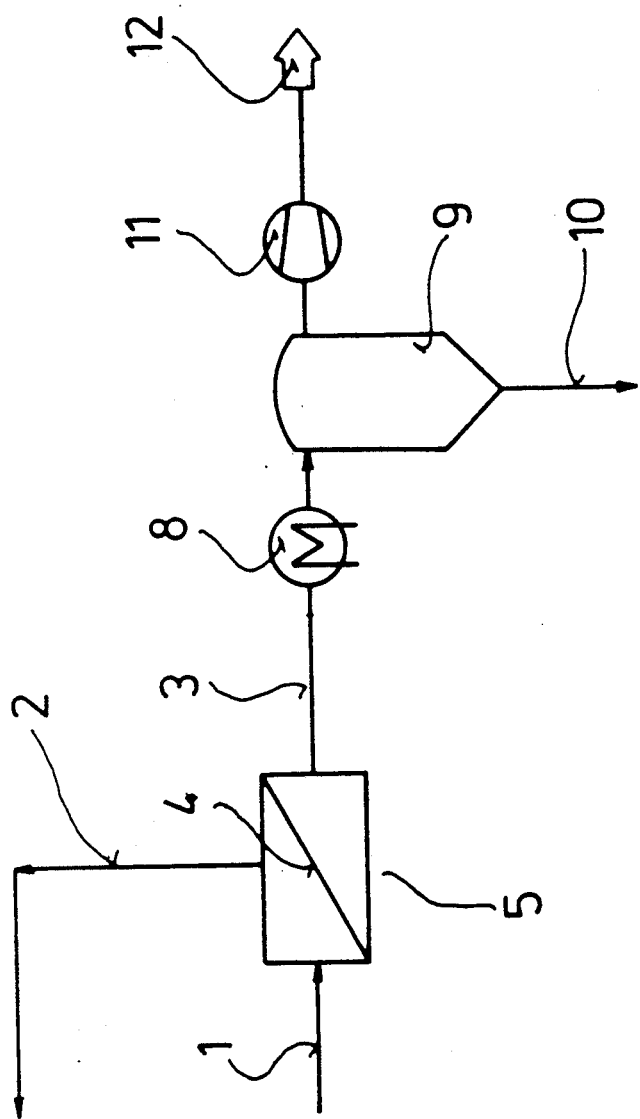

In FIG. 2, the permeate vapor passes via line 3 into a heat exchanger 8, where it is cooled down, and the condensate obtained is collected in vessel 9 and discharged via line 10. A small noncondensable bleed stream is conducted away with the pressure-regulated vacuum pump 11 via line 12, the pressure preset by the vacuum pump being advantageously higher than the vapor pressure of the condensate. In general, the pressure preset by the vacuum pump is from 1 to 200 mbar, preferably from 1 to 100 mbar, in particular from 1 to 50 mbar, higher than the vapor pressure of the condensate and lower than the vapor pressure of the feed mixture. The permeate pressure and hence its influence on the selectivity of the separation and thus on the permeate composition is determined in this form of the process by the vapor pressure of the permeate at the condensation temperature. The temperature of the feed mixture in this process is in general within the range from 20° to 150° C., preferably from 60° to 100° C., in particular from 70° to 90° C.

Figure 3:
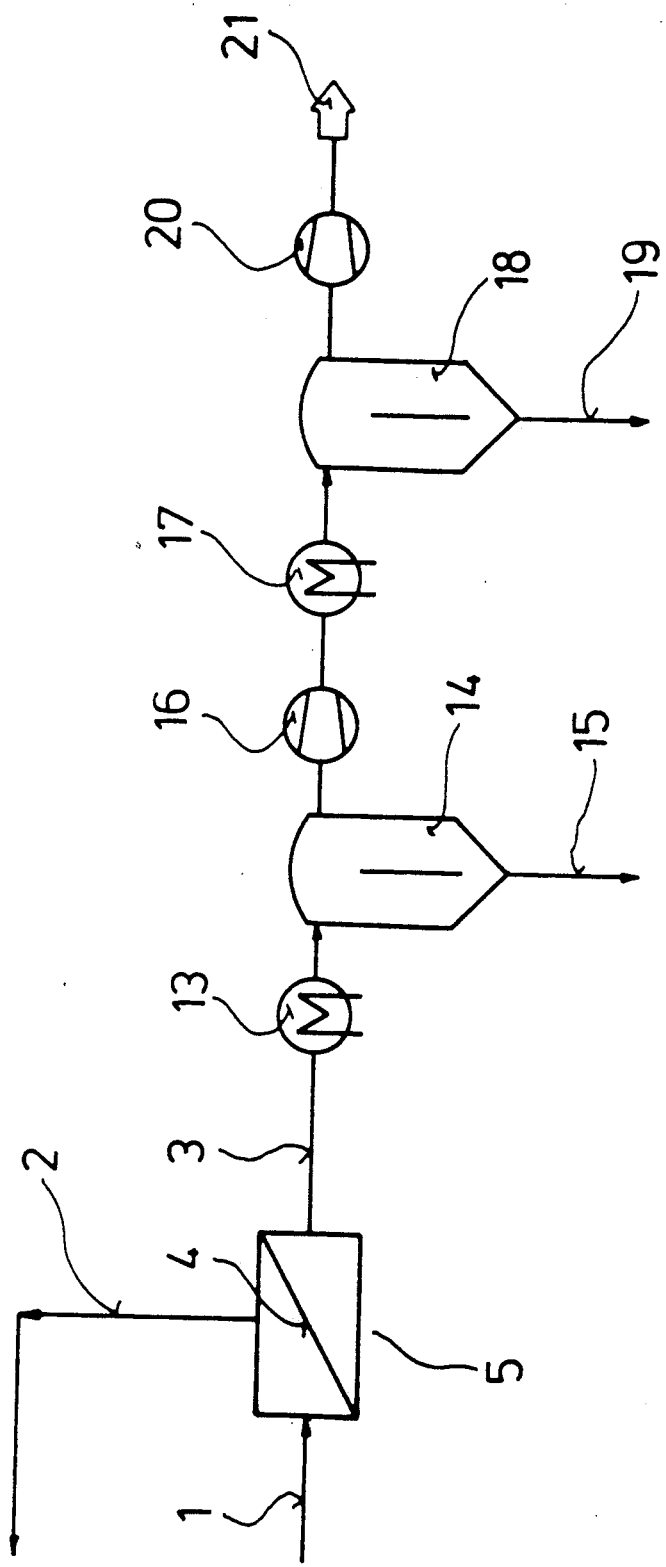

According to FIG. 3, the permeate vapor, having passed through line 3 and cooled down in the heat exchanger 13, partially condenses out in the vessel 14, and the partial condensate is withdrawn via line 15. The uncondensed portion of the permeate is then compressed in the pressure-regulated compressor 16 and, after cooling down the second heat exchanger 17, condensed in the vessel 18 and withdrawn via line 19. The noncondensable remainder of the permeate is transported away with the further pressure-regulated compressor 20 via line 21. This manner of permeate removal and treatment makes it possible to divide up the permeate into a plurality of partial condensates having different compositions, the quantities of the partial condensates and their composition being variable within wide limits through the choice of pressures and condensation temperatures, so that the permeate can be fractionated in a simple manner. If a plurality of condensation stages are used, their number is in general from 2 to 5, preferably 2 or 3.

Alternatively to the procedure of FIG. 3, the permeate can also be compressed in multiple stages, passing on whichever permeate vapor remains. If a plurality of compression stages are employed, their number is in general from 2 to 5, preferably 2 or 3.

One embodiment of the process according to the present invention comprises for example using a water/$CO_2$/monoalkylamine stream obtained as a recycle stream in a process for preparing dialkylureas by reacting monoalkylamines with $CO_2$ in a reaction zone at elevated temperature and pressure and separating the unconverted monoalkylamine and $CO_2$ and the water formed from the dialkylurea formed and recycling the removed unconverted monoalkylamine and $CO_2$ and any water remaining after the water separation stage into the reaction zone in the recycle stream.

The monoalkylamine and $CO_2$ starting materials for preparing dialkylureas are generally used in an amount of from 2 to 5 mol, preferably from 2 to 3 mol, of monoalkylamine per mole of $CO_2$. Preferred monoalkylamines are those of from 1 to 8, preferably from 1 to 4, carbon atoms, e.g. methylamine, ethylamine, propylamine, isobutylamine and hexylamine. The reaction is in general carried out at from 150° to 220° C., preferably at from 180° to 200° C., and at from 30 to 160 bar, preferably from 100 to 150 bar, preferably continuously.

After the reaction has ended, the uncoverted starting materials are separated from the dialkylurea, in general by depressurizing and heating, and recycled into the reactor in a recycle stream containing the monoalkylamine, $CO_2$ and water. To prevent the concentration of the water of reaction in the recycle stream from rising to too high a level, the recycle stream is subjected as a whole or in part to the process for removing water by pervaporation according to the present invention, which produces a permeate having a higher water concentration and a lower $CO_2$ and monoalkylamine concentration than the recycle stream prior to pervaporation. Accordingly, the retentate withdrawn from the pervaporator and recycled to the reactor has a lower water concentration and a higher $CO_2$ and monoalkylamine concentration than the recycle stream prior to pervaporation.

The permeate, which in addition to the main constituent water also contains a minor concentration of $CO_2$ and monoalkylamine, is advantageously treated with an alkali metal hydroxide solution, preferably sodium hydroxide solution, e.g. aqueous 10–25% strength by weight sodium hydroxide solution, to recover the monoalkylamine; the amounts of alkali metal hydroxide used relative to the amount of $CO_2$ to be bound being stoichiometric or in excess, for example in a 1.1-fold excess relative to the stoichiometric quantity.

The treatment of the permeate with the alkali metal hydroxide solution is in general carried out at from 80° to 130° C., preferably from 90° to 110° C., and at from 1 to 3 bar, advantageously by employing a distillation column for example by passing the permeate into the middle portion of the distillation column while the alkali metal hydroxide solution is introduced at the top of the column. The monoalkylamine is withdrawn at the top of the column and advantageously recycled into the reactor for conversion to dialkylurea. The bottom product of the column is an aqueous carbonate solution which contains the $CO_2$ in a bound form and water.

The Examples which follow illustrate the present invention.

EXAMPLE 1

In a process for reacting methylamine with $CO_2$ to give dimethylurea in a pressure reactor, the unconverted methylamine and $CO_2$ and the water formed are separated from the dimethylurea product to leave a recycle stream consisting of 45% by weight of methylamine (free methylamine and carbamate methylamine), 28% by weight of $CO_2$ (dissolved $CO_2$ and carbamate $CO_2$) and 27% by weight of water. To prevent the water concentration of the recycle stream returned into the pressure reactor from being raised to too high a level by the water of reaction, the recycle stream is subjected to a pervaporation process at 80° C. at a permeate pressure of 20 mbar using a solution diffusion membrane based on a polyvinyl alcohol, the membrane area used measuring 250 m$^2$, giving a 132 kg/h permeate stream consisting of 76% by weight of water, 3% by weight of $CO_2$ and 21% by weight of methylamine. The permeate stream thus removes water from the recycle stream at a rate of 100 kg/h. The retentate obtained from the pervaporation process is returned as remaining recycle stream into the pressure reactor.

To recover the methylamine the permeate stream is then passed into the middle portion of a distillation column into which aqueous sodium hydroxide solution is introduced at the top at a rate of 7.2 kg of NaOH/h for binding the $CO_2$. The bottom product withdrawn from the column is an aqueous sodium carbonate solution. The top of the column produce is methylamine, which is recycled into the pressure reactor for conversion to dimethylurea.

COMPARATIVE TRIAL

The reaction of Example 1 is repeated and again leaves a recycle stream consisting of 45% by weight of methylamine, 28% by weight of $CO_2$ and 27% by weight of water.

To remove water from the recycle stream at a rate of 100 kg/h, a bleed stream of 370 kg/h is withdrawn from the recycle stream by the known process and passed for recovery of the methylamine into the middle portion of a distillation column into which aqueous sodium hydroxide solution is introduced at the top at a rate of 188 kg of NaOH/h for binding the $CO_2$. The bottom product is aqueous sodium carbonate solution and the top product is methylamine, which is recycled into the pressure reactor.

The comparative trial consumes with 188 kg of NaOH/h an amount of NaOH which is 26 times higher than that required in the process of Example 1 according to the present invention. Accordingly, the process according to the present invention produces a significantly smaller amount of aqueous sodium carbonate solution, so that a significantly smaller quantity of aqueous sodium carbonate solution has to be worked up or disposed of.

EXAMPLE 2

A recycle stream of the composition of Example 1 (45% by weight of methylamine, 28% by weight of $CO_2$ and 27% by weight of water) is subjected to a pervaporation process according to FIG. 1 in a pervaporator according to Example 1 in which the permeate is withdrawn in vapor form via line 7. The permeate obtained has a composition of 74% by weight of water, 4% by weight of $CO_2$ and 22% by weight of methylamine at a predetermined permeate pressure of 30 mbar. If the predetermined permeate pressure is increased to 100 mbar, the permeate obtained has a composition of 58% by weight of water, 9% by weight of $CO_2$ and 33% by weight of methylamine.

EXAMPLE 3

A recycle stream having the composition of Example 1 is subjected to a pervaporation process according to FIG. 3 in a pervaporator according to Example 1 at 80° C. Initially vaporous permeate then passes through two condensation stages in accordance with FIG. 3.

In the first condensation stage, a pressure of 50 mbar is predetermined with the vacuum pump 16, and a condensation temperature of 0° C. (case 1) in heat exchanger 13 gives 94% by weight of the total permeate as condensate stream 15 of the composition 71% by weight of water, 9% by weight of $CO_2$ and 20% by weight of methylamine. If the condensation temperature of 20° C. is set in heat exchanger 13 (case 2), unchanged pressure will convert 87% by weight of the permeate, based on the total permeate, in the first condensation stage into condensate of composition 80% by weight of water, 6% by weight of $CO_2$ and 14% by weight of methylamine, obtained via line 15.

The second condensation stage is set in both cases (case 1 and case 2) in heat exchanger 17 to a condensation temperature of 0° C. and a pressure of 1 bar. These conditions produce in both cases the remaining permeate portions as condensate via line 19. In case 1 the amount of condensate in the second condensation stage is about 6% by weight and in case 2 about 13% by weight, each percentage being based on the original amount of permeate obtained via line 13, and in both cases the condensate is virtually 100% methylamine.

We claim:

1. A process for removing water from a mixture containing water, $CO_2$ and one or more amines by pervaporation which comprises: bringing the mixture into contact with one side of a membrane and removing the water-containing permeate as a vapor from the other side of the membrane.

2. A process as defined in claim 1, wherein a water-selective membrane is used.

3. A process as defined in claim 1, wherein the membrane has an active layer based on polyvinyl alcohol.

4. A process as defined in claim 1, wherein the permeate is condensed and conducted away in liquid form.

5. A process as defined in claim 1, wherein the permeate is compressed and/or condensed in a plurality of downstream stages, the individual compression and/or condensation stages being maintained under different pressures and/or temperatures.

6. A process as defined in claim 1, wherein water is separated from a stream containing water, $CO_2$ and a monoalkylamine, obtained as a recycle stream in a process for preparing a dialkylurea by reacting a monoalkylamine with $CO_2$ in a reaction zone at elevated temperature and pressure, and separating the unconverted monoalkylamine and $CO_2$ and the water formed from the dialkylurea formed and recycling the removed unconverted monoalkylamine and $CO_2$ and any water remaining after the water separation stage into the reaction zone in the recycle stream.

7. A process as defined in claim 6, wherein the monoalkylamine is methylamine and the dialkylurea is dimethylurea.

* * * * *